United States Patent [19]

Leonard

[11] 4,211,009
[45] Jul. 8, 1980

[54] DENTAL HANDPIECE
[75] Inventor: Henri Leonard, Besancon, France
[73] Assignee: Micro-Mega S.A., Besancon, France
[21] Appl. No.: 867,099
[22] Filed: Jan. 5, 1978
[30] Foreign Application Priority Data
   Feb. 3, 1977 [FR] France .................. 77 04027
[51] Int. Cl.² ........................... A61C 1/10
[52] U.S. Cl. .......................... 433/126; 433/133
[58] Field of Search .......... 403/348, 349; 32/26, 32/27

[56] References Cited
U.S. PATENT DOCUMENTS

| 1,741,969 | 12/1929 | Bellows | 403/348 |
| 3,423,781 | 1/1969 | Henson | 403/349 |
| 3,909,946 | 10/1975 | Watanabe | 32/27 |

Primary Examiner—Robert Peshock
Attorney, Agent, or Firm—Robert E. Burns; Emmanuel J. Lobato; Bruce L. Adams

[57] ABSTRACT

A dental handpiece comprises a rear portion or handle and a front portion or head which are coupled by means of a female member secured to one portion and a male member secured to the other portion, the female member having formed therein a longitudinal slot and a recess shifted angularly in relation to the slot, the male member comprising a projection, one member comprising an elastically deformable portion whereby rotating one member in relation to the other through a predetermined angle permits introducing said projection into the recess, the projection being allowed to expand therein.

11 Claims, 13 Drawing Figures

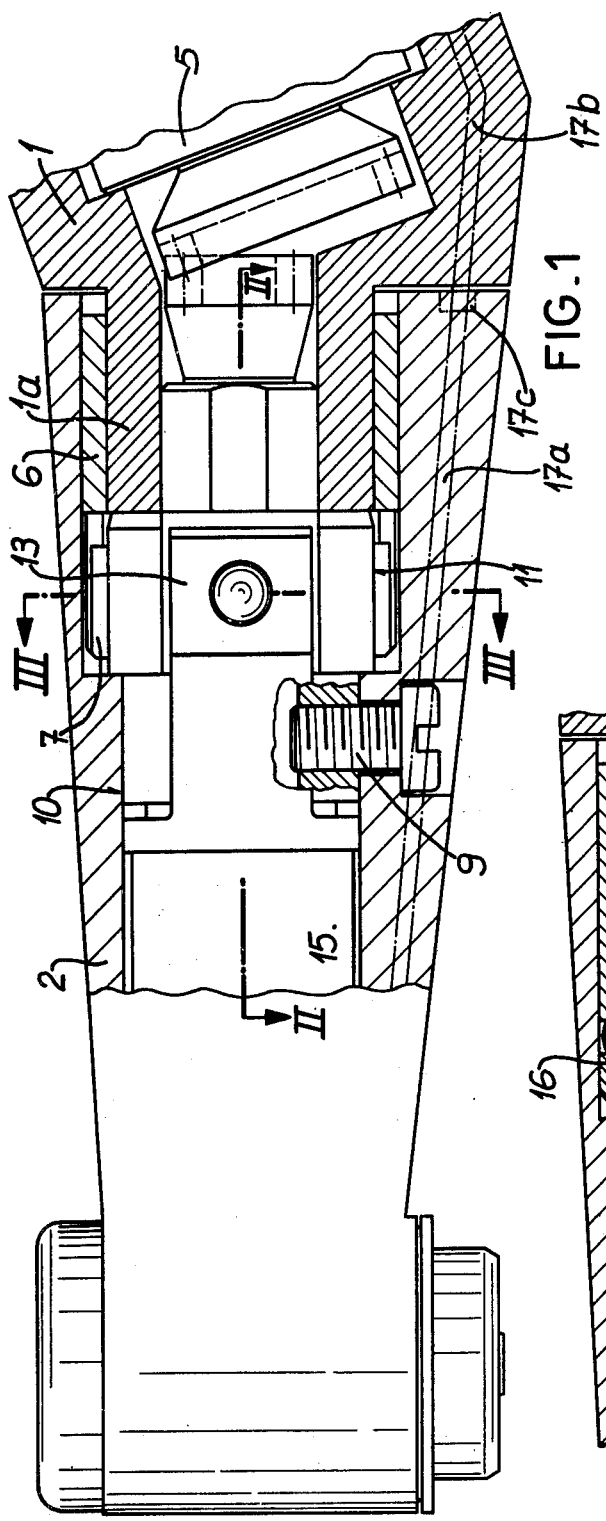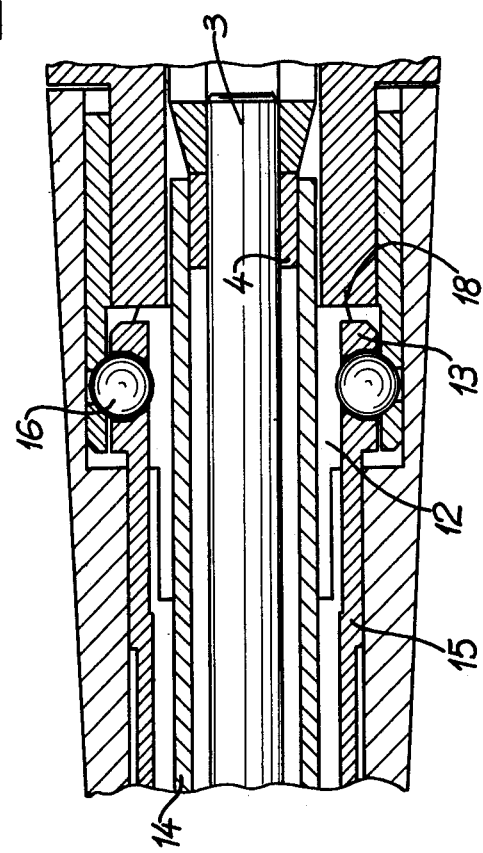

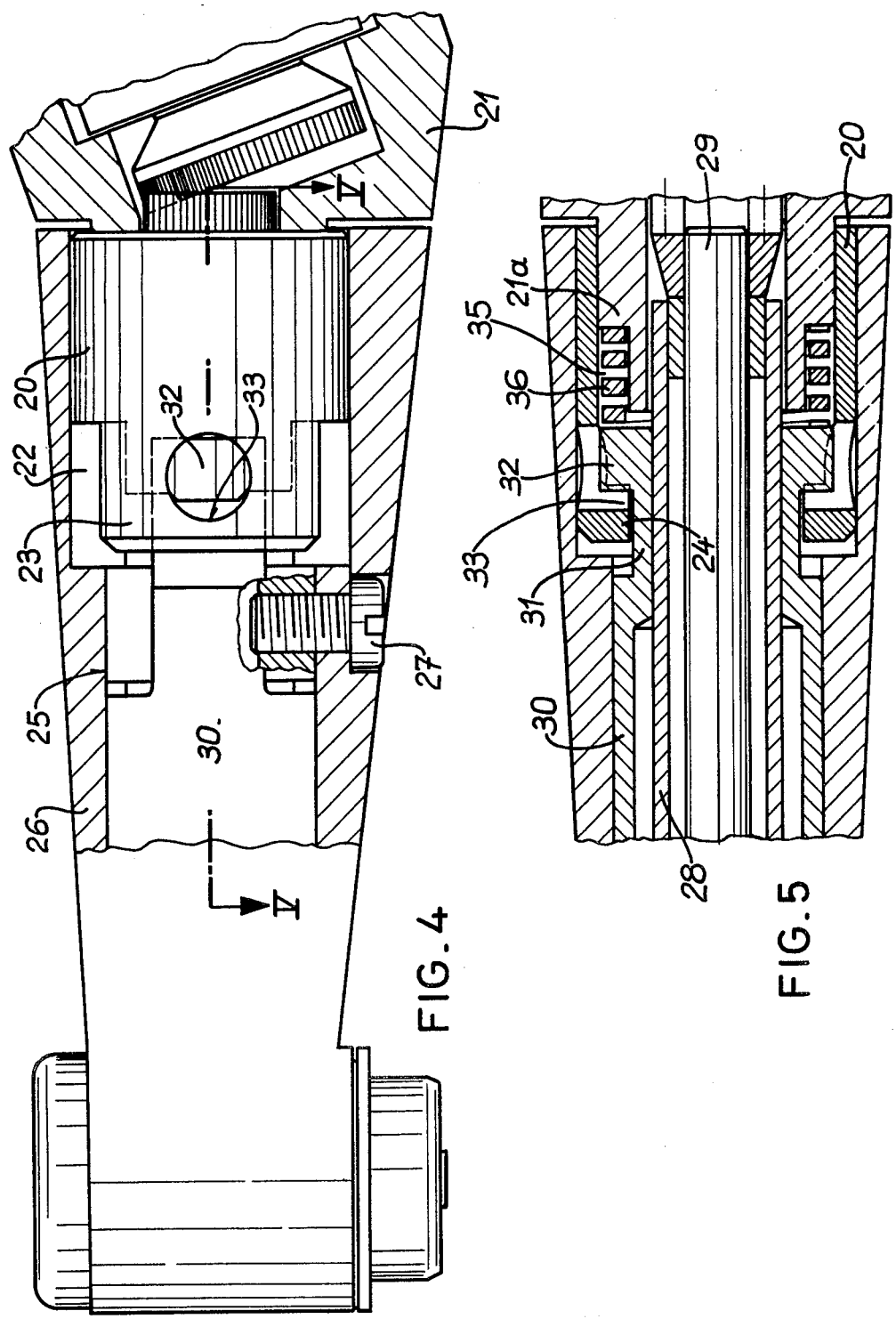

DENTAL HANDPIECE

FIELD OF THE INVENTION

The present invention relates in general to dental handpieces and has specific reference to an improved handpiece of this type comprising a rear portion or handle and a front portion or head, and means for coupling these portions to each other.

DESCRIPTION OF THE PRIOR ART

Dental handpieces are already known wherein the head is secured by means of a spring-bolt to the handle of the instrument, this bolt being secured for instance on the handle and resiliently engaging one or several suitable holes formed on the rear end of the head. The bolt is released by means of a push-button accessible from outside and so arranged that depressing this button will release the bolt.

However, this arrangement is objectionable in that after several actuations the rigidity of the coupling is impaired due to the loss of elasticity of the spring, so that in the long run a detrimental play is likely to develop between the two parts. On the other hand, with this type of coupling the release button projects from the surface of the hand tool holder and this may prove not only inconvenient for the dentist but also detrimental to the aesthetics of the instrument.

In other instances, the coupling is obtained simply by screwing the two parts to each other, and this obviously requires more time; besides, with this type of coupling an accurate mutual angular positioning of the two parts is precluded and this may constitute a serious drawback in case it is desired to provide an internal conduit or passage through the wall of the hand tool holder, for example a passage for a liquid to be atomized against the tool for cooling it.

DESCRIPTION OF THE INVENTION

It is the primary object of the present invention to provide an improved dental handpiece incorporating a novel and particularly simple coupling arrangement which, inter alia, affords a very accurate angular positioning of the rear portion of the hand tool holder in relation to the other front portion thereof.

For this purpose, the dental handpiece according to this invention is characterized in that said coupling means comprise on the one hand a female member secured to one of the two portions, which consists of a socket in which at least one longitudinal slot opening on the free end of the socket is formed, at least one recess being formed in the socket wall and shifted angularly in relation to said slot, and on the other hand a male member secured to the other portion, adapted to fit in said female member and comprising adjacent its free end at least one projection of a section engaging at least partially said slot, said male and/or female elements comprising a resiliently deformable portion whereby when engaging said male member into said female member from a position such that said projection engages said slot, moving one member in relation to the other member causes said projection to penetrate into said socket, the two members being locked in relation to each other when said projection registers with said recess.

Thus, a coupling is obtained which affords a rapid assembling of the two portions with each other this assembling being obtained by applying a relatively moderate torque to the parts involved. Besides, with this type of coupling the two portions can be positioned very accurately in relation to each other and may therefore advantageously be provided with an internal passage or conduit for supplying cooling water or other liquid to the head of the holder. Moreover, this coupling is completely enclosed and therefore a hand tool holder having a perfectly smooth or plain outer surface can be obtained, this eliminating any unsightly or inconvenient projection. On the other hand, this coupling may be used on all handpieces, whether straight or bent (such as obtuse-angled holders).

A clearer understanding of this invention will be had if reference is made to the attached drawing when reading the following description of typical embodiments, given by way of example, of the invention. In the drawing:

BRIEF DESCRIPTION OF THE DRAWING

FIG. 1 is a side elevational view with fragmentary sections showing on a larger scale a first form of embodiment of the dental handpiece according to this invention;

FIG. 2 is a longitudinal section taken along the line II—II of FIG. 1;

FIG. 4. is a side elevational view with fragmentary sections of a second form of embodiment of the handpiece according to this invention;

FIG. 5 is a longitudinal section taken along the line V—V of FIG. 4;

DESCRIPTION OF THE PREFERRED EMBODIMENTS

Figure 1A:
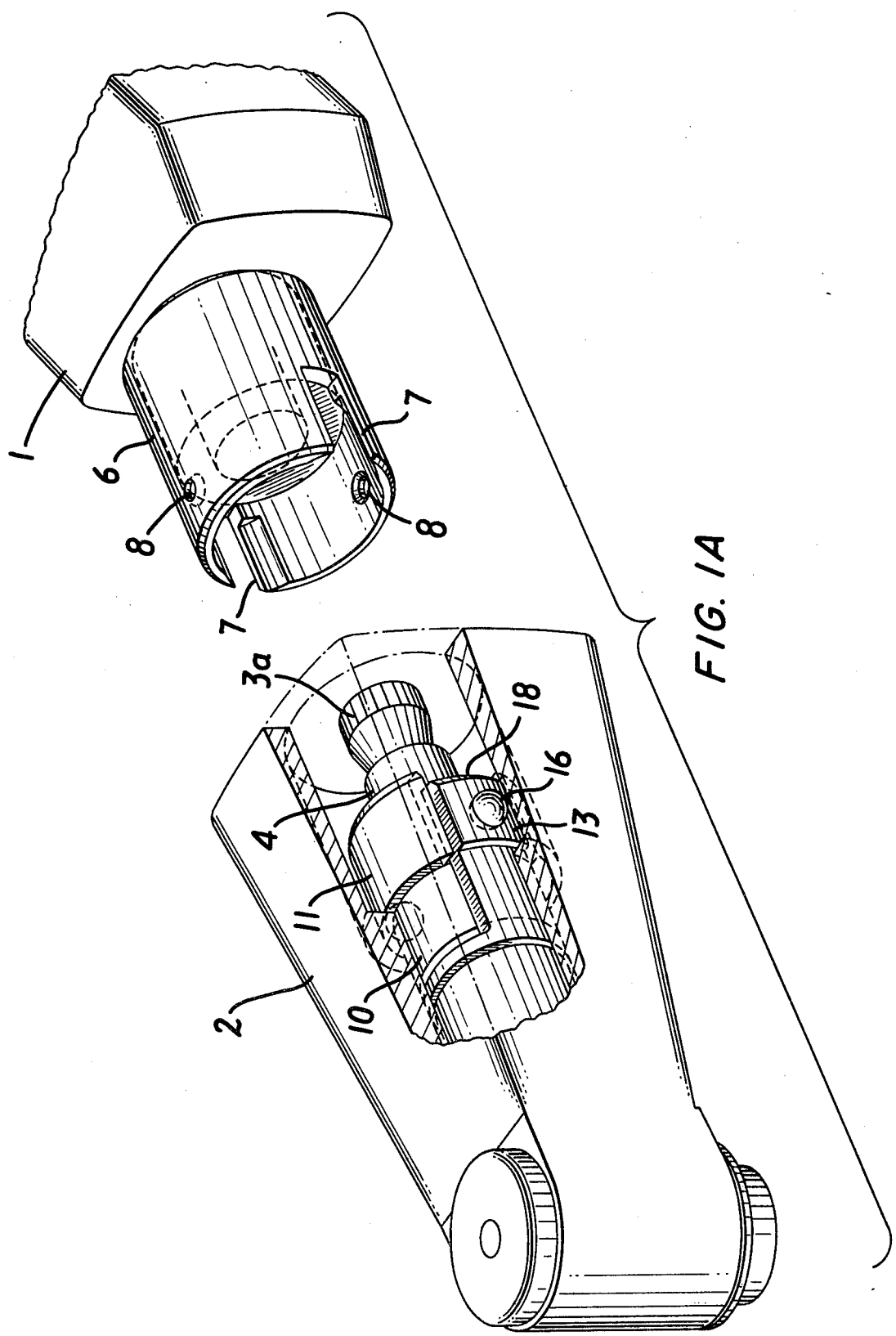
FIG. 1A is an exploded perspective view of the embodiment shown in FIG. 1.
Figure 3:
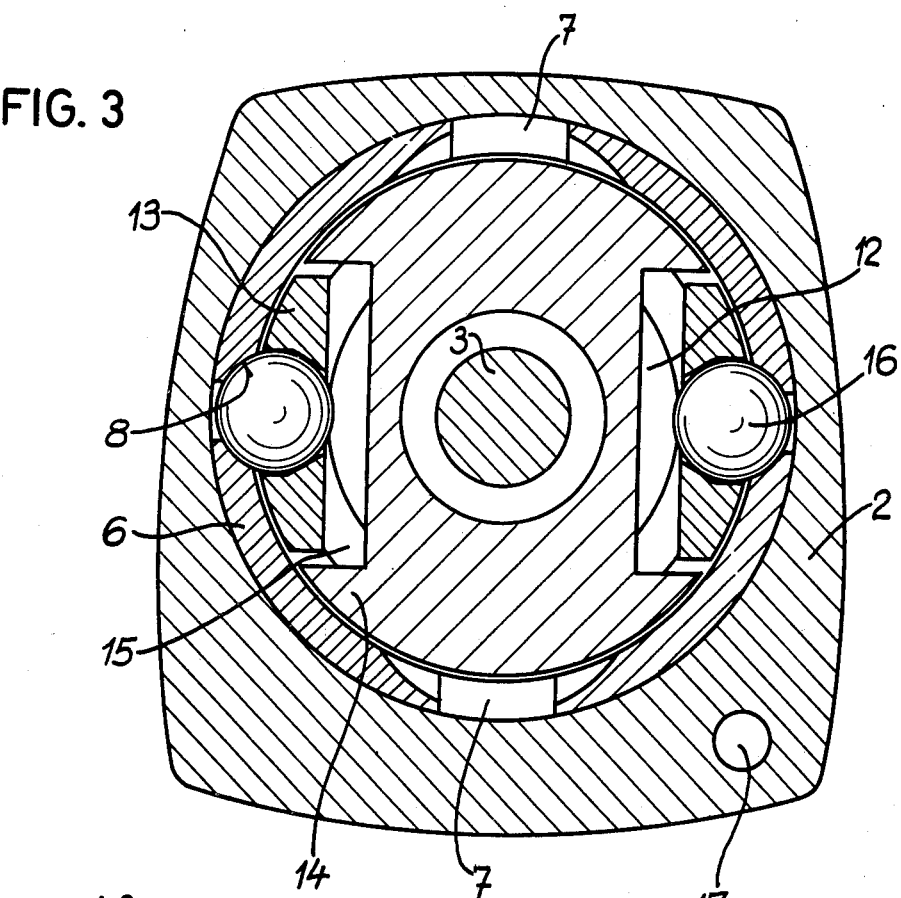
FIG. 3 is a cross section taken on a larger scale along the line III—III of FIG. 1.

Referring first to FIGS. 1 to 3 of the drawing, the dental handpiece illustrated therein comprises two portions, namely a rear portion 1 or handle and a front portion 2 or head, the latter being adapted to have a milling cutter or other tool (not shown) secured therein as conventional in the art. A rotary central shaft 3 for driving the tool is mounted in the front section 2 and supported at its rear end by a plain bearing 4; furthermore, to this rear end of shaft 3 is fitted a coupling 3a by means of which the shaft is coupled to the main driving shaft 5 in the known fashion.

The front end of rear portion 1 comprises an extension 1a of reduced diameter to which a socket 6 constituting the female member of the coupling is force fitted. The free end of this socket is provided with a pair of diametrally opposite longitudinal slots 7, the inner wall of socket 6, which bounds these slots, being bevelled. Formed in the walls of socket 6 which extend between the slots 7 is a central recess 8 of part-spherical configuration, disposed in the axial direction between the bottom of slots 7 and the free end of the socket. Thus, a pair of diametrally opposite recesses 8 and a pair of diametrally opposite slots 7, respectively, are provided.

The front portion 2 having substantially the shape of a hollow socket is secured for example by means of a screw 9 to a male member 10 of substantially cylindrical configuration and adapted to fit in said socket 6. This male member 10 comprises a cylindrical shoulder 11 having substantially the same diameter as the inner diameter of socket 6, so that said male member can fit freely in said socket 6, the radial face 18 of this shoulder limiting the length of penetration of the male member 10 into the socket 6. A pair of diametrally opposite axial grooves 12 are cut in said shoulder 11 and adapted to constitute recesses engageable by corresponding resilient lugs or arms 13. To facilitate the manufacture of the parts, this male member consists preferably of two sections force fitted into each other, i.e., one inner section 14 having an axial bore permitting the free passage of shaft 3 and being provided with said shoulder 11, and an outer section 15 force fitted on the inner section 14 and provided with the pair of diametrally opposite resilient lugs 13 of which the free thicker end engages said axial grooves 12 while being kept somewhat spaced from the bottom of these grooves when a radial force is applied to said lugs. Crimped in the free and thicker end of each lug 13 is a steel ball 16 projecting from the surface of shoulder 11, the radius of each ball 16 being substantially equal to the radius of the part-spherical central recesses 8.

For coupling the rear portion 1 to the front portion 2 of the holder, it is thus only necessary to introduce the male member 10 as far as possible into the socket 6 so as to position the lugs 13 with their balls 16 in proper alignment with the socket slots 7, then to rotate with a slight torque the male member 10 with respect to the socket 6 through an angle of about 90°. During this movement, the balls 16 slide within the socket due to the elasticity of lugs 13 which move inwardly into the grooves 12 until the balls register with the recesses 8 in which they drop as a consequence of the expansion of said lugs 13. The sliding movement of balls 16 in socket 6 is facilitated by the bevelled edges of slots 7.

The spherical configuration of balls 16 and recesses 8 affords a compensation of the axial and radial forces, thus ensuring a perfect stability of the coupling.

To separate the two portions of the handpiece it is only necessary to exert on one of them a torque of same magnitude in one or the other direction in order to cause the balls to emerge from their corresponding recesses and bring them in proper registration with the slots 7 in which they can expand.

This type of coupling is particularly advantageous whenever it is contemplated to provide an internal passage or conduit in the handpiece for a fluid, for instance a cooling liquid to be atomized against the tool at the working point thereof. In this case, the front portion 2 is provided with a longitudinal passage 17a which should be perfectly aligned with another longitudinal passage 17b formed in the rear portion 1, and with the above-described coupling these two portions can be positioned in very accurate alignment with each other in order to cause said passages to be co-extensive, the fluid-tightness at the coupling joint being provided by a seal 17c fitted in a cavity surrounding the end of one of the passages.

Reference will now be made to FIGS. 4 to 7 of the drawing illustrating a second form of embodiment of the coupling according to the instant invention. In this case, the socket 20 force fitted on the end of the rear portion 21 is also provided with a pair of diametrally opposite axial slots 22 bounding two arcuate lugs 23 terminating with an in-turned projection or flange 24 of part-circular configuration. The in-turned portion of said projection has a part-circular cavity 33 formed therein; however, to facilitate the manufacture of the component elements, this cavity 33 is obtained by simply forming a circular hole 33a through the lug 23.

The male member 25 secured to the front portion 26 of the handpiece, for example by means of a screw 27, also consists of two interfitting pieces, namely an internal tubular member 28 through which the central shaft 29 extends freely, and an external member 30 force fitted on the tubular inner member 28 provided with a pair of diametrally opposite lugs 31. The shaft 29 is coupled to the main drive shaft by a coupling 29a. The end of each lug constitutes an arcuate boss 32 having its edges nearest to the head of the front portion slightly bevelled or rounded. On the other hand, this male member 25 has two diametrally opposite flat faces 34 formed thereon, said flat faces 34 being spaced angularly by 90° with respect to the bosses 32. The thickness of the male element 25, measured between these two flat faces 34, corresponds approximately to the distance measured between the two in-turned projections 24 of socket 20.

Between this socket 20 and sleeve 21a of the rear portion 21 to which said socket is secured, an annular groove 35 is formed for receiving a helical compression spring 36.

To couple the rear portion 21 to the front portion 26 of the handpiece, the operator simply introduces the male member 25 into the socket 20 by aligning the slots 22 with the bosses 32 and therefore the flat faces 34 with the projections 34; then, the male member 25 is forced into socket 20 against the resistance of spring 36 and the male member 25 is pivoted through 90° with respect to the socket 20 until the bosses 32 register with recesses 33 into which they are snappily engaged by the force of spring 36. Due to the provision of rounded edges on bosses 32, it is only necessary to exert a slight torque for causing the bosses 32 to slide between the lugs 23 of socket 20.

Figure 9:
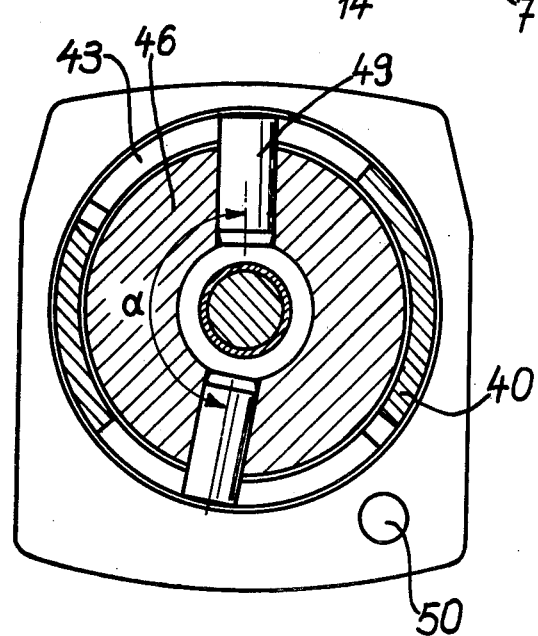
FIG. 9 is a cross section taken along the line IX—IX of FIG. 8.
Figure 4A:
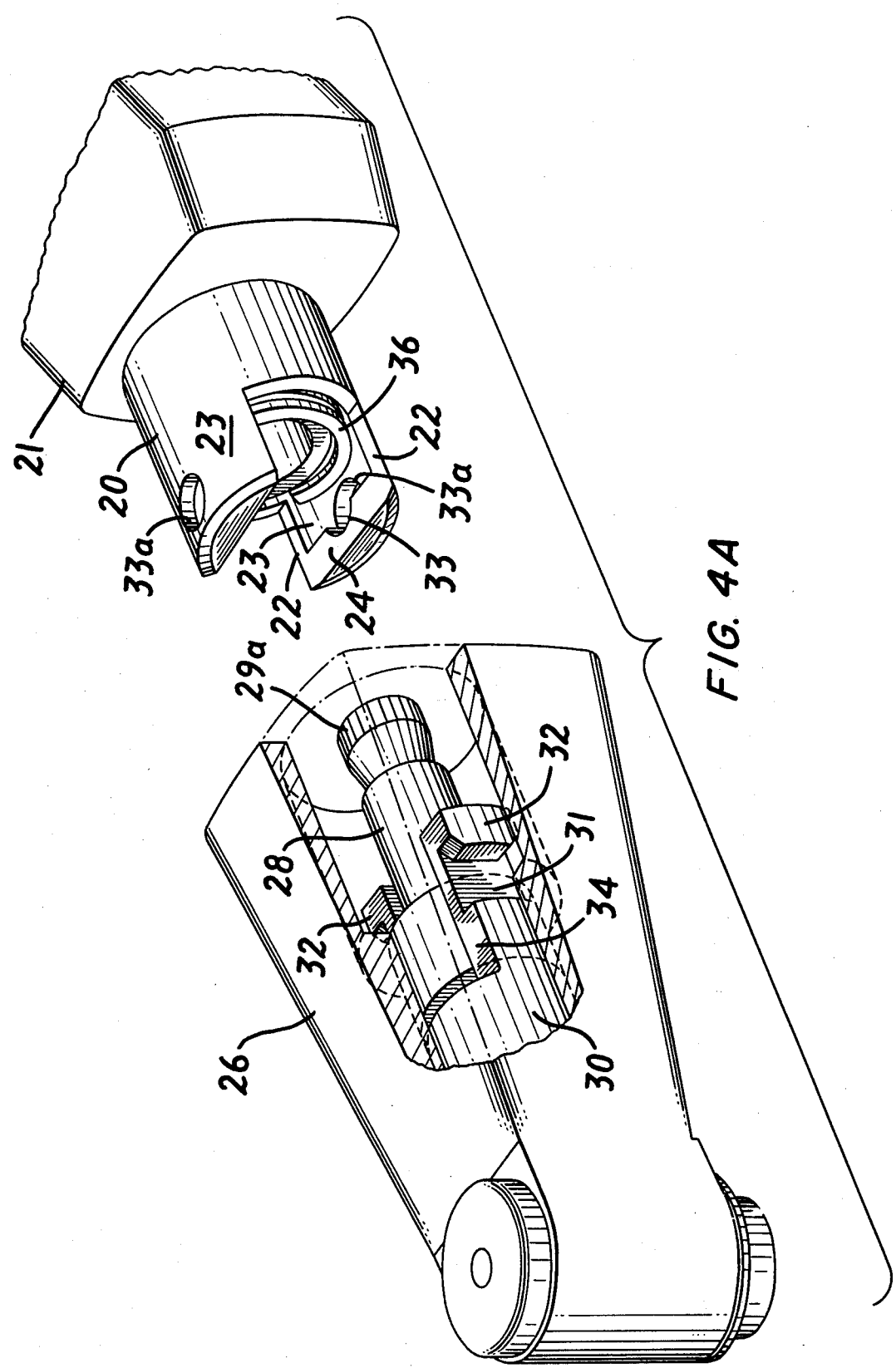
FIG. 4A is an exploded perspective view of the embodiment shown in FIG. 4.
Figure 6:
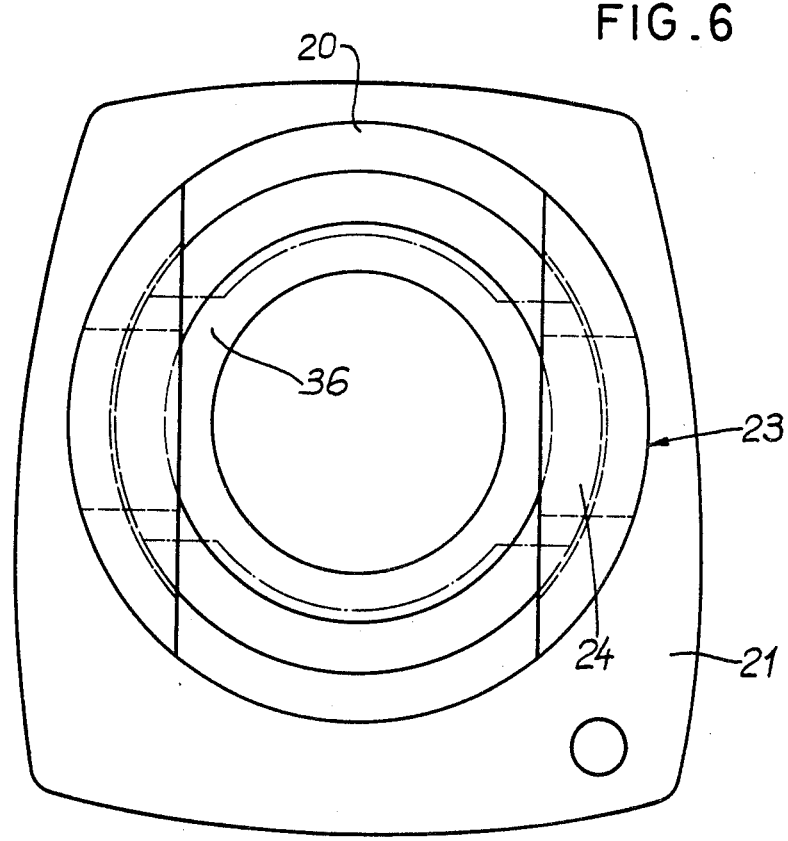
FIG. 6 is an end view of the rear portion of the holder, provided with the socket and the male member shown in phantom lines.
Figure 7:
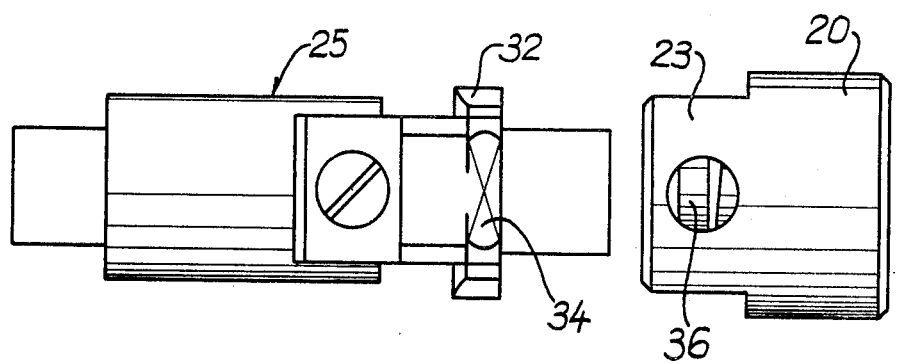
FIG. 7 is a side elevational view showing the two members of the coupling before the assembling thereof.
Figure 8:
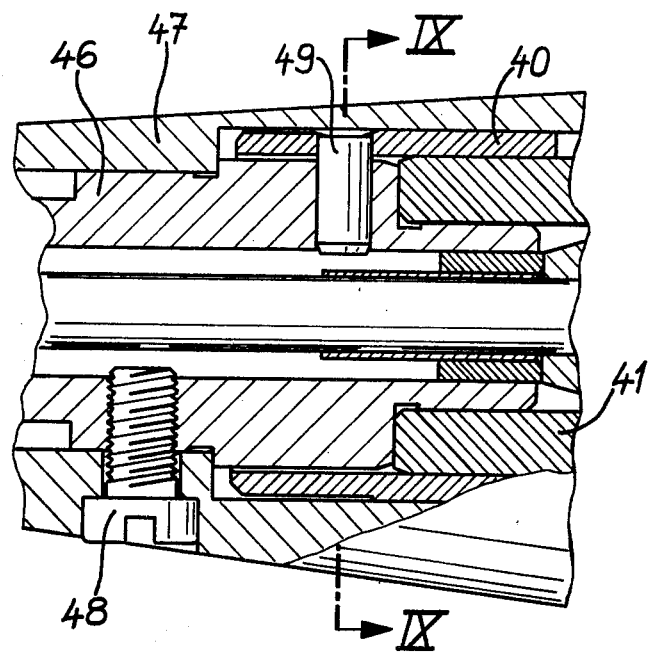
FIG. 8 is a side elevational view with fragmentary sections showing a third form of embodiment of a handpiece according to this invention.
Figure 10:
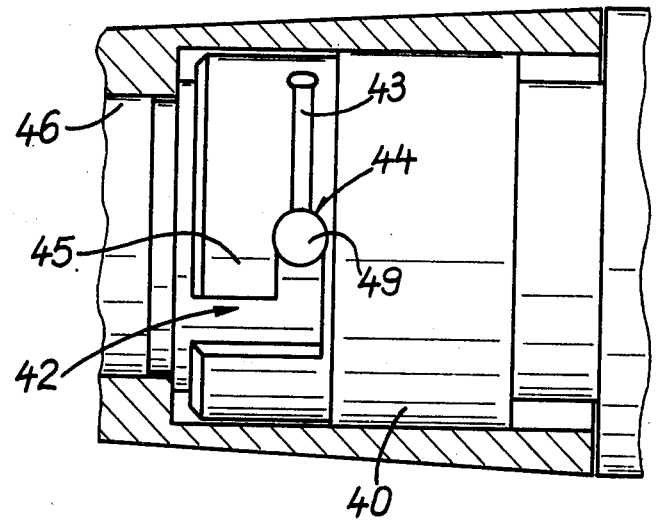
FIG. 10 is a plane view from above of the embodiment shown in FIG. 8 with a fragmentary section.
Figure 8A:
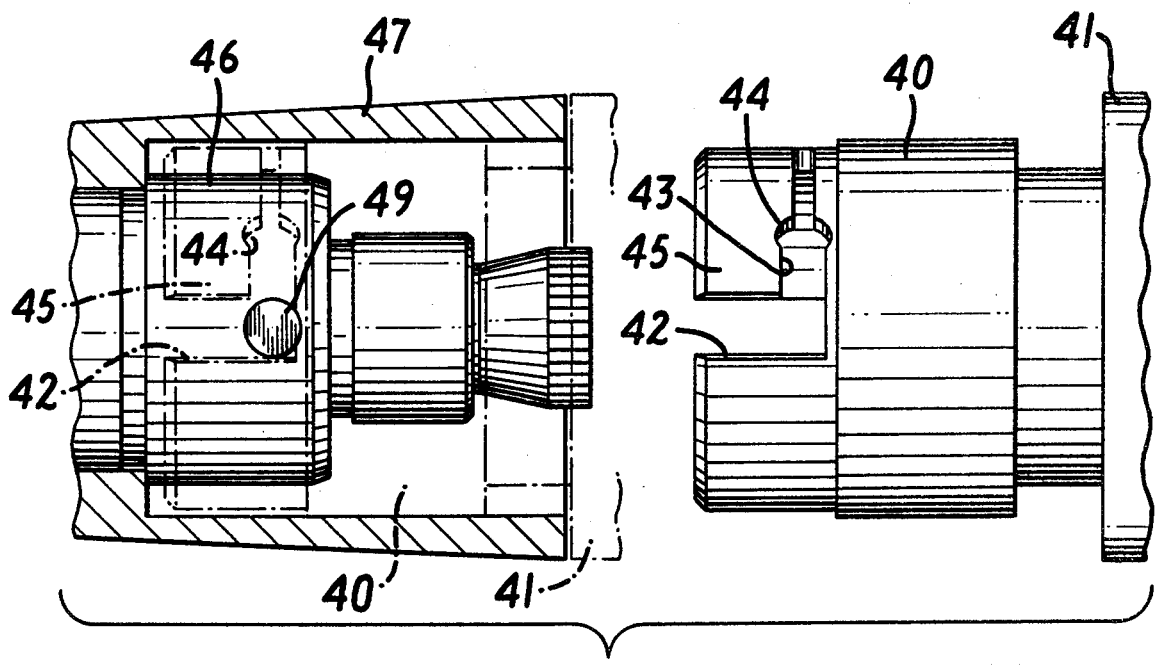
FIG. 8A is an exploded view of the embodiment shown in FIG. 8.

Referring now to FIGS. 8 to 10 of the drawing which illustrate a third form of embodiment of the invention, it will be seen that the socket 40 force fitted on the end of the rear portion 41 of the holder is provided with a pair of longitudinal slots 42 opening perpendicularly into two transverse peripheral slots 43. These slots 43 consist of two portions of different widths, the portion facing the closed end of the slot being narrower than the portion facing the open end thereof, both portions being interconnected by an arcuate recess 44 having a diameter slightly greater than the width of the widest portion of said slot. Both slots 42 and 43 provide at the end of socket 40 a pair of resilient lugs 45.

The male member 46 secured to the front portion 47, for example by means of a screw 48, comprises a pair of cylindrical studs 49 projecting from its outer surface, the diameter of studs 49 being equal to the diameter of the arcuate recesses 44. The studs 49 are disposed in a same radial plane but on different radii, so that their axes (see FIG. 9) form an angle α slightly smaller than 180°. Likewise, the two longitudinal slots 42 and the two arcuate recesses 44 are not diametrally opposite, but form between them the same angle α slightly smaller than 180°, respectively, in order to provide only one possible angular relative position between the male and female members and thus ensure an accurate alignment between the inner passages 50 possibly formed in the two portions.

When coupling the two portions with each other, the male member 46 is introduced into the socket 40, and studs 49 are inserted into the longtiudinal grooves 42, whereafter the two portions are rotated in relation to each other until the studs 49 engage the arcuate recesses 44, this being permitted by the elastic distortion of resilient arms or lugs 45.

According to a preferred form of embodiment of this invention, the angular shift between the longitudinal slots 42 and the arcuate recesses 44 may be of the order of 30°.

Other modifications and changes may be contemplated when carrying out the present invention, without inasmuch departing from the basic principles thereof, notably in connection with the number and shape of the projections and their recesses.

What is claimed is:

1. A dental handpiece comprising a rear portion and a front portion, and means for coupling said portions to each other, said coupling means comprising a female member secured to one of said two portions and comprising a socket having a pair of longitudinal slots opening to the free end of said socket, with arcuate wall portions between said slots and inwardly facing recesses in said wall portions spaced from the free end of said socket, and a male member secured to the other of said two portions and comprising a pair of resilient arms positioned to be received in said slots of said socket and a radially outwardly projecting protuberance on each of said arms positioned to be received in said recesses of said socket when said male member is rotated with respect to said female member, said resilient arms being flexible in a radial direction to press said protuberances into said recesses, whereby said female member and male member are coupled with one another by inserting said arms of said male member into said slots of said socket and then rotating said male member relative to said female member to bring said protuberances into said recesses.

2. A dental handpiece according to claim 1, wherein said recesses are part-spherical and said protuberances are balls fixed on said arms.

3. A dental handpiece according to claim 1, wherein edges of said longitudinal slots are bevelled inwardly to facilitate said protuberances riding over said edges when said male member is rotated relative to said female member.

4. A dental handpiece according to claim 1, wherein said male member comprises two parts force-fitted to one another, namely an inner cylindrical part having a pair of longitudinal grooves and an outer part having a collar portion force-fitted on said inner part and a pair longitudinally projecting resilient arms received in said grooves and spaced from the bottoms of said grooves.

5. A dental handpiece comprising a rear portion and a front portion, and means for coupling said portions to each other, said coupling means comprising a female member secured to one of said two portions and comprising a socket having a pair of longitudinal slots opening to the free end of said socket and arcuate wall portions between said slots, said wall portions having radially in turned flanges at the open end of said socket with a cavity on the axially inner face of each of said flanges, and a male member secured to the other of said two portions and comprising a tubular member with a pair of radially outwardly projecting lugs positioned to be received in said slots of said socket in a first position of said male members relative to said female member and to be received in said cavities when said male member is rotated to a second position relative to said female member, and means for resiliently pressing said lugs into said cavities in said second position, whereby said female member and male member are coupled with one another by inserting said male member into said socket with said lugs received in said slots against the resistance of said resilient means and then rotating said male member relative to said female member to bring said lugs into position to be received in said cavities whereupon said lugs are pressed into said cavities by said resilient means.

6. A dental handpiece according to claim 5, wherein said cavities comprise holes extending radially through said arcuate wall portions.

7. A dental handpiece according to claim 5, in which faces of said lugs facing said cavities are rounded to be received in said cavities and to ride out of said cavities when said male member is rotated from said second position relative to said female member.

8. A dental handpiece according to claim 5, wherein said socket has an annular groove and said resilient means comprises a coil spring received in said groove and pressing against the end of said male member when inserted into said socket.

9. A dental handpiece comprising a rear portion and a front portion, and means for coupling said portions to each other, said coupling means comprising a female member secured to one of said two portions and comprising a socket having a pair of longitudinal slots opening to the free end of said socket and a peripheral slot extending circumferentially from the inner end of each of said slots, said peripheral slots defining resilient arm portions between said peripheral slots and the end of said socket, each of said peripheral slots comprising a wider first portion, a narrower second portion and an enlargement in said first portion at the opening of said second portion, and a male member secured to the other of said two portions and comprising a tubular portion of a size to be received in said socket and radially outwardly projecting studs positioned to be received in said longitudinal slots of said socket in a first rotational position of said male member relative to said female member and to be received in said peripheral slots upon rotation of said male member to a second position relative to said female member, said studs having a diameter corresponding to said enlargement and slightly greater than the width of said first portion of said peripheral slot, whereby said female and male members are coupled with one another by inserting said male member in said socket with said studs received in said longitudinal slots and then rotating said male member relative to said female member to bring said studs into said enlargements of said first portions of said peripheral slots, movement of said studs through said first portions of said peripheral slots being permitted by the flexing of said resilient arm portions defined by said peripheral slots.

10. A dental handpiece according to claim 9, wherein said longitudinal slots in said socket are disposed at an angle of less than 180° to one another, and said studs of said male member are disposed at the same angle relative to one another, so that said male member can be inserted in said female member in only one rotational position.

11. A dental handpiece according to claim 9, wherein said enlargements are formed by arcuate recesses in the sides of said first portions of said peripheral slots in said socket.

* * * * *